United States Patent [19]

Sjöberg

[11] Patent Number: 5,250,004
[45] Date of Patent: Oct. 5, 1993

[54] DEVICE FOR WITHDRAWING BLOOD FROM SLAUGHTER ANIMALS

[75] Inventor: John A. Sjöberg, Smygehamn, Sweden

[73] Assignee: Anitec-John Sjoberg AB, Malmo, Sweden

[21] Appl. No.: 776,406
[22] PCT Filed: May 22, 1989
[86] PCT No.: PCT/SE89/00284
    § 371 Date: Nov. 22, 1991
    § 102(e) Date: Nov. 22, 1991
[87] PCT Pub. No.: WO90/14013
    PCT Pub. Date: Nov. 29, 1990
[51] Int. Cl.$^5$ ............................................. A22B 5/04
[52] U.S. Cl. ........................................ 452/65; 452/67
[58] Field of Search ............................ 452/65, 67, 69

[56] References Cited

U.S. PATENT DOCUMENTS

| | | | |
|---|---|---|---|
| 3,292,206 | 12/1966 | Rizzi | 17/1 |
| 3,649,996 | 3/1972 | Marti | 17/1 C |
| 3,947,919 | 4/1976 | Ekdahl | 452/69 |
| 4,617,700 | 10/1986 | Ba'Torfalui et al. | 452/69 |

FOREIGN PATENT DOCUMENTS

| | | | |
|---|---|---|---|
| 130671 | 3/1975 | Denmark. | |
| 821467 | 11/1951 | Fed. Rep. of Germany. | |
| 870957 | 3/1953 | Fed. Rep. of Germany. | |
| 130671 | 3/1975 | Fed. Rep. of Germany. | |
| 205063 | 12/1983 | Fed. Rep. of Germany | 452/65 |
| 379142 | 9/1975 | Sweden. | |
| 7309982 | 9/1975 | Switzerland. | |
| 465163 | 3/1975 | U.S.S.R. | 452/69 |

Primary Examiner—Willis Little
Attorney, Agent, or Firm—Cushman, Darby & Cushman

[57] ABSTRACT

A device for withdrawing blood from slaughter animals transported on a conveyor serially past a sticking station has a debleeding carousel (1) disposed at the sticking station and consisting of a body (2), a lower frame member (3) and an upper member frame (4), which frame members are synchronously rotatable on a vertical shaft (5) of the body, a number of collecting vessels (6) mounted on the lower frame member around the vertical shaft, a number of hollow knives (7) corresponding to the number of collecting vessels and suspendible around the vertical shaft each in a holder (9) on the upper frame member, and a hose (8) extending between each hollow knife and the associated collecting vessel for conducting blood from the hollow knife to the collecting vessel. The debleeding carousel is rotatable in such steps that the holders are displaced between a number of stopping positions around the vertical shaft, the distance between the stopping positions being equal to the distance between the holders. A sensor is fixedly mounted on the body opposite one of the stopping positions and adapted to sense the displacement of a hollow knife in a holder located in this stopping position, in order upon such displacement to initiate rotation of the carousel one step.

11 Claims, 5 Drawing Sheets

Blood withdrawing zone

DEVICE FOR WITHDRAWING BLOOD FROM SLAUGHTER ANIMALS

The present invention relates to a device for withdrawing blood from slaughter animals transported on a conveyor serially past a sticking station. The device has a carousel which is disposed at the sticking station and includes a body, a lower frame member and an upper frame member, said frame members being synchronously rotatable on a verticle shaft of said body, a number of collecting vessels mounted on the lower frame member around said vertical shaft, a number of hollow knives corresponding to the number of collecting vessels and suspendible around the vertical shaft each in a holder on said upper frame member, and a hose extending between each hollow knife and the associated collecting vessel for conducting blood from the hollow knife to the collecting vessel.

Today, the slaughtering of animals in slaughterhouses demands high efficiency, hygienic conditions and adequate control of the slaughtered animals. Withdrawing blood from the animals for use in the manufacture of foods is part of the activities in a slaughterhouse. The demands mentioned above are of course also placed on this activity.

When extracting blood from animals, the extracted blood coagulates within a very short time. To prevent this, an anticoagulant is added. The anticoagulant must be added in an amount proportional to the amount of extracted blood. Too low a dose will not prevent coagulation, and too high a dose means that the limit values according to current food legislation may be exceeded.

To comply with hygienic standards, the withdrawal of blood for food production purposes requires the insertion of a probe-like object provided with a knife blade, a so-called hollow knife, in the stunned or anaesthetised animal. Perforating the aorta and/or major blood vessels results in a debleeding which makes the animal die within a short time. To comply with hygienic standards, the blood withdrawn by means of a hollow knife must be conducted in a close system, such as a hose, to a vessel provided with a cover, e.g. of the carousel type. This makes it more difficult for the sticker to check visually that a sufficient amount of blood debleeds to ensure that the anaesthetised animal will not become conscious before dying.

To provide rational and hygienically acceptable extraction of blood for food production purposes, sticking or debleeding carousels of different designs have been devised and patented. However, because of technical deficiencies and inadequate compliance with veterinary requirements, these installations have been put into practice to a limited extent only.

DE 821,467 and 870,957, and U.S. Pat. No. 3,649,996 describe carousels of this type. The arrangements described in these documents are all integrated in the slaughtering line by providing a loop in the slaughtering line, inside of which the sticking carousel is disposed. The animals are transported hanging from a conveyor, and carriers are provided at the top of the carousel in order, during the rotation of the carousel, to engage the hooks on which the animals are hanging. Blood collecting vessels are arranged at the lower part of the carousel and are each connected to a hollow knife.

One drawback of the known arrangements is that they cannot be used for slaughter animals which are lying. Another drawback is that the slaughtering line must be modified to provide said loop. Thus, great efforts are needed for shifting the carousel to another slaughtering line or to another location on the slaughtering line. Finally, the known constructions have no means for automatically washing or cleaning the hol'ow knife and the blood collecting vessels.

The primary object of the present invention is to provide a fully automatic sticking carousel which is able in a highly efficient manner to comply with today's requirements in respect of yield and hygienic standards when extracting blood for food production purposes and which can be adapted to different slaughtering lines without any modification thereof, and which, finally, can be used for both lying and hanging slaughter animals.

A second object of the invention is to provide a sticking carousel, the speed of which is automatically adjusted to the speed of the conveyor transporting the animals.

A third object is to provide a sticking carousel in which the supply or dosage of anticoagulent is synchronised with the speed of rotation of the carousel and, thus, the slaughtering speed.

A fourth object is to provide a sticking carousel in which the addition of anticoagulent is effected only when blood is actually withdrawn from an animal, whereby if there is a void in the slaughtering line and one or more of the knives of the sticking carousel are not used, no anticoagulant will be dosed.

A fifth object is to provide a sticking carousel with automatic washing and sterilisation of the equipment included in the carousel.

A sixth object is to provide a sticking carousel having means for monitoring the amount of blood withdrawn from each animal.

A seventh object of the invention is to provide a sticking carousel which is connected to a double discharge system passing blood from the collecting vessels on to larger storage vessels.

According to the invention, these objects are achieved by means of a device stated in the introduction to this specification and having the features recited in the accompanying claims.

The device according to the invention offers several advantages. The sticking carousel can be disposed at any location adjacent a slaughtering line without any modification of the slaughtering line. The sticking carousel is autonomous and, if need be, can be shifted to another slaughtering line. Thanks to the automation of the sticking carousel, one sticker and one helper are enough for handling a slaughtering speed of up to 900 hogs per hour.

The device according to the invention can be directly connected to storage vessels for the extracted blood, which may be disposed on a floor underneath the slaughtering line and the sticking carousel. As an alternative, the carousel can be connected to the storage vessels via pumps and equaliser tanks. In this case, the storage vessels can be disposed on the same level as the sticking carousel and the slaughtering line.

There is a common washing or cleaning system for the sticking carousel, the storage vessels, the conduits connecting the sticking carousel to the storage vessels, and the equaliser tanks. This system being no part of the invention, it will be only briefly described below.

With the device according to the invention, it is possible to supply anticoagulant in a reliable manner. This is done by means which ensure the supply of anticoagulant to the hollow knife during the period or time when blood is passing through the hollow knife and the hose and into the collecting vessel.

The invention will now be described in more detail hereinbelow in an embodiment with reference to the accompanying drawings.

FIG. 1A schematically shows a part of a plant including an embodiment of the device according to the invention.

FIG. 1A schematically shows another part of the plant.

FIG. 2 schematically shows the sticking carousel and more specifically illustrates the means for supplying an anticoagulant to the hollow knife.

FIG. 3b shows an alternative embodiment of the arrangement in FIG. 3a.

Figure 4:
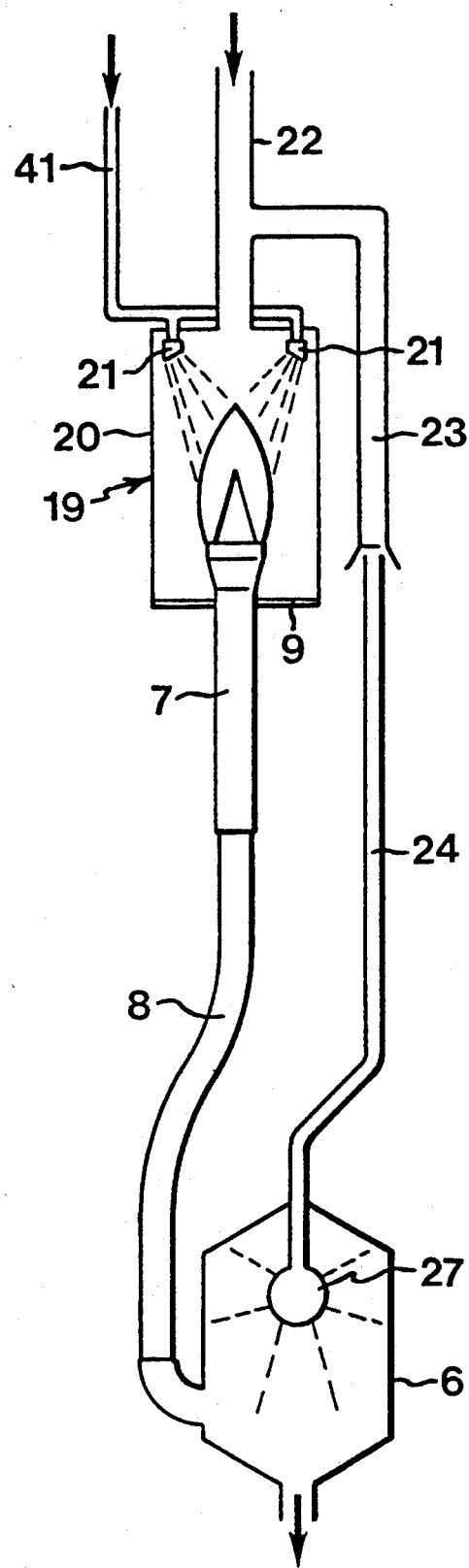

FIG. 4 schematically shows a washing or cleaning unit for the hollow knife, hose and collecting vessel.

Figure 5:
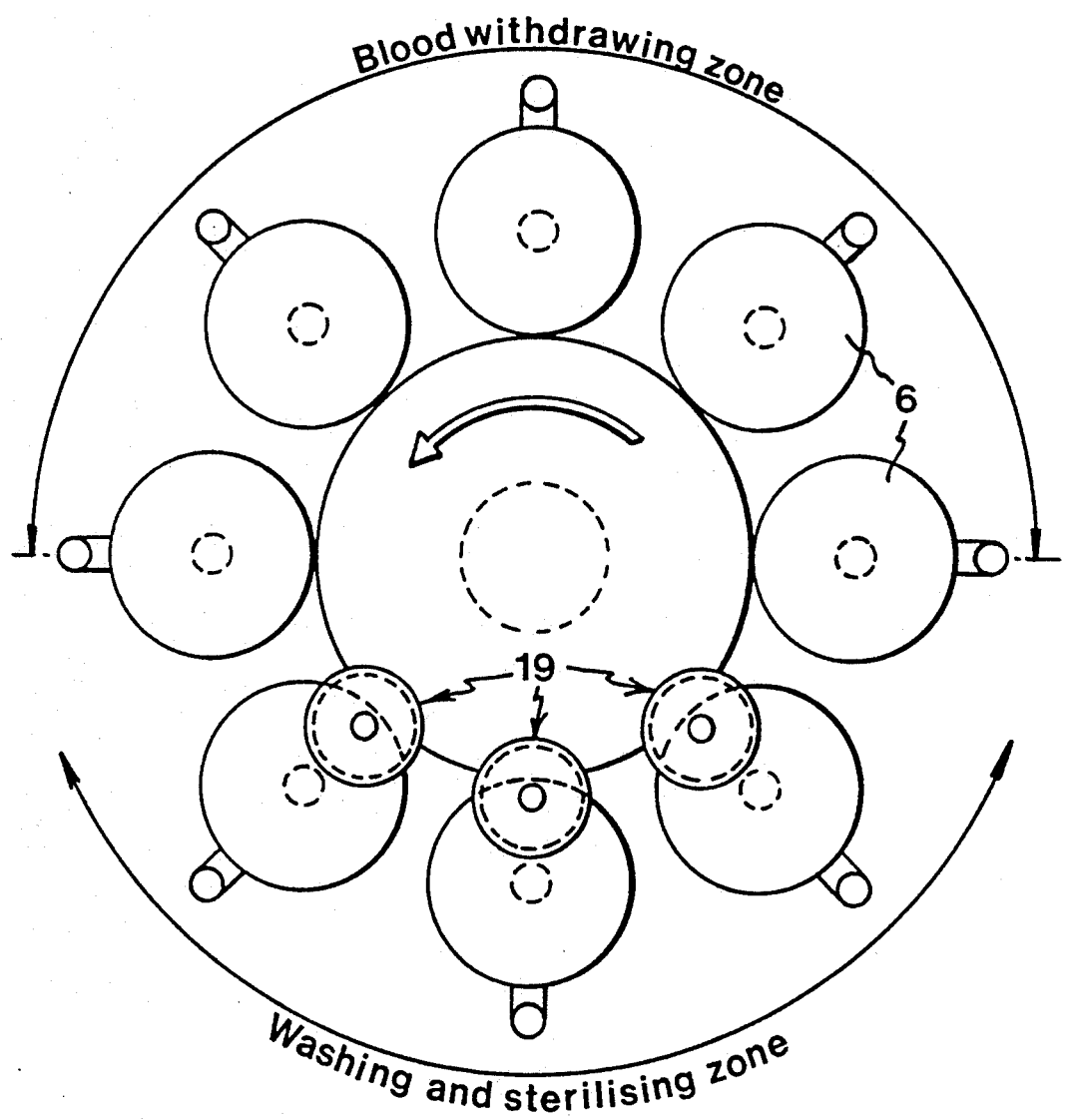

FIG. 5 is a top plan view showing the location of the washing or cleaning unit in the sticking carousel.

Figure 1A:
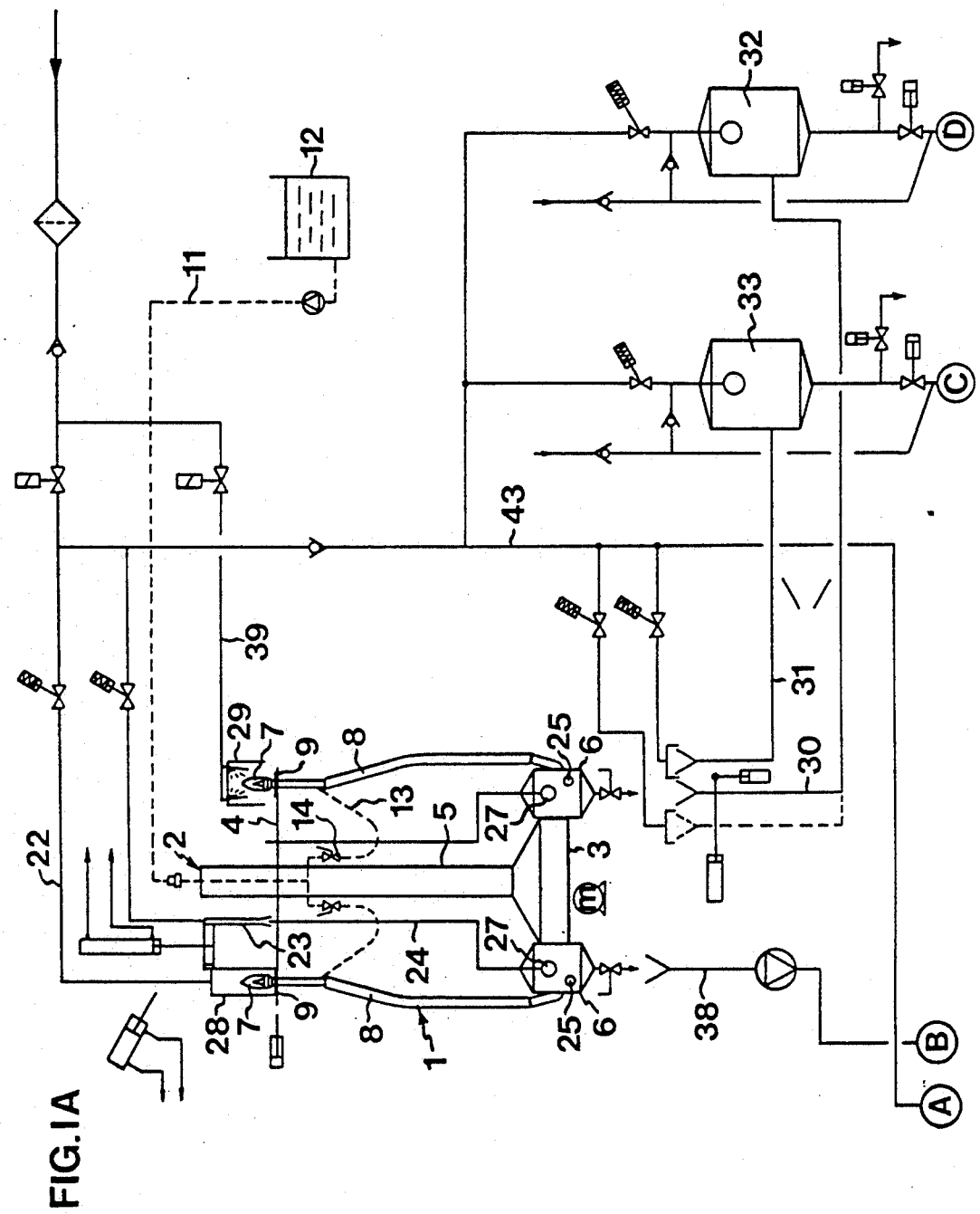

FIG. 1A shows an example of a device according to the invention when connected in a plant for withdrawing blood from slaughter animals. The device includes a sticking carousel 1 disposed at a conveyor (not shown) on which slaughter animals are conveyed in a succession. The sticking carousel has a body 2 with a vertical shaft 5. The body has a rotatable lower frame member 3 and a rotatable upper frame member 4. The frame members are rotatable in synchronism with each other by means of a motor. On the lower frame member, there are mounted a number of blood collecting vessels 6, e.g. four, six or eight vessels. FIG. 1A shows only two collecting vessels 6. A hollow knife 7 is connected to each collecting vessel through a hose 8. When the hollow knife is not in use, it is suspended in a holder 9 on the upper frame member 4. The sticking carousel is rotated stepwise on the shaft 5. It is rotated one step when a knife has been removed from the animal after use and placed in its holder. To this end, a sensor is mounted on the sticking carousel.

Figure 2:
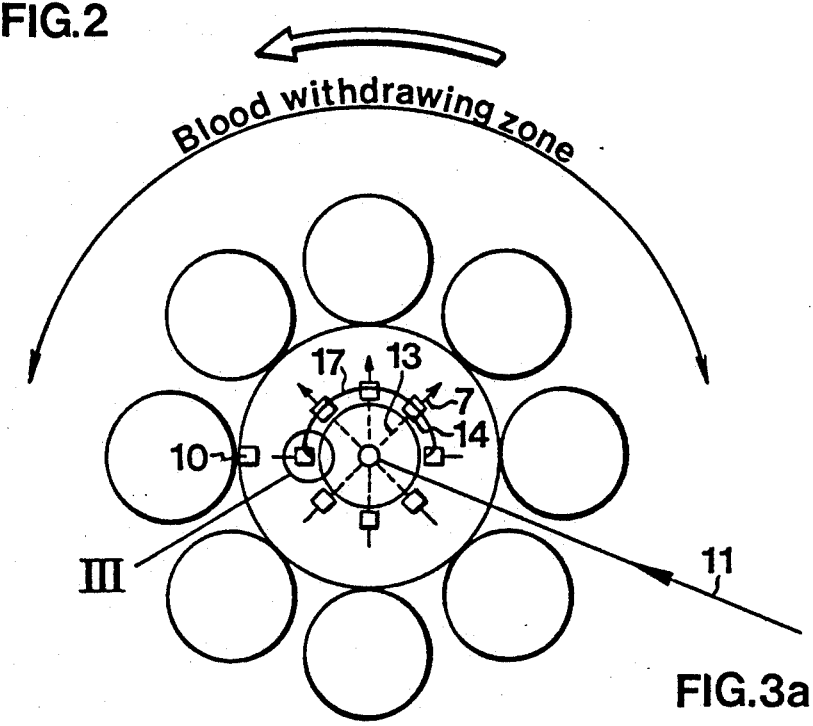

FIG. 2 illustrates a blood withdrawing zone. At the beginning of this zone, the hollow knife is unhooked from its holder and stuck into an animal passing by, and at the end of the zone the knife is again placed in its holder which during the blood withdrawing operation has been rotated about half a revolution.

The stepwise rotation of the sticking carousel is carried out such that each step corresponds to the distance between two consecutive holders. This means that the holders will during the operation of the carousel will come to a number of stopping positions corresponding to the number of holders. The stepwise rotation of the carousel is initiated by the sensor 10, schematically indicated in FIG. 2. The sensor has been disposed at the last stopping position in the blood withdrawing zone and senses the point of time when the hollow knife is placed in the holder. When this is done, the sensor emits a signal to a control system (not shown) which orders the motor to rotate the sticking carousel one step. By controlling the stepwise rotation of the sticking carousel in this manner, the speed at which the animals are transported on the conveyor is automatically taken into account. Thus, the stepwise rotation of the sticking carousel is automatically synchronised with the speed of the conveyor.

FIG. 1A also shows a level or quantity sensor 25 mounted in each collecting vessel. This sensor monitors the amount of blood which has flown into the collecting vessel. If this amount does not reach a threshold value, the sensor will emit an alarm signal to the control system which calls the sticker's attention to the fact that the hollow knife 7 has not been correctly stuck into the animal.

To prevent the blood from coagulating, an anticoagulant supply unit is connected to the sticking carousel. This unit consists of a store of anticoagulant 12, a conduit 11 extending between the store 12 and the sticking carousel 1, and flexible hoses 13 connected to the conduit 11 through a rotary coupling and each connected to a hollow knife 7. A valve arrangement 14 is mounted on each hose 13. This valve arrangement will be described in more detail in connection with the description of FIGS. 2 and 3.

When a collecting vessel has been moved out of the blood withdrawing zone, it comes to a position above one of two discharge conduits 30 and 31. In FIG. 1A, a collecting vessel 6 is located above the first discharge conduit 30. The collecting vessel 6, containing blood from a single animal, discharges into the first discharge conduit 30 through which the blood passes into a first equaliser tank 32 and from there on to one of three first storage vessels 36a–c. The discharge is effected by means of a first pump 34. The pump is activated when a level indicator in the equaliser tank indicates that the amount of blood in the equaliser tank has exceeded a predetermined value. The other system for discharging blood into the second discharge conduit 31, the second equaliser tank 33, the second pump 35 and the second storage vessels 37a–c of course operates in the same way as the first discharge system consisting of the first discharge conduit 30, the first equaliser tank 32, the first pump 34 and the first storage vessels 36a–c. The advantage of using two discharge systems is that continuous operation can be achieved. Thus, the blood withdrawing operation need not be interrupted when the discharge system should be cleaned upon completion of a so-called batch.

When the hollow knives are located outside the blood withdrawing zone, the hollow knife 7 is flushed or sterilised. In FIG. 1A, sterilisation is performed in a steriliser 29 including a tunnel through which the hollow knives pass and which has two spray nozzles supplied with sterilising liquid from a conduit 39.

Between two batches, not only the hollow knife 7, but also the hose 8 and the collecting vessel 6 are washed. This is done by means of a washing box 28 which is lowered over the hollow knife 7 and supplies cleaning liquid through the hollow knife, the hose and down into the collecting vessel 6. Further, a pipe 23 is lowerable together with the washing box 28 for docking a pipe 24 which is connected to the washing box and which in the collecting vessel opens in a spray nozzle 27. The cleaning liquid is discharged from the collecting vessel into a drain conduit 38.

FIG. 2 shows schematically and from above the sticking carousel and the means connected to it for supplying an anticoagulant to the hollow knives. As mentioned above, a conduit 11 from a store of anticoagulant is connected to the sticking carousel through a rotary coupling. From the rotary coupling extends a flexible hose 13 to each hollow knife 7. The valve arrangement 14 is symbolised by a square at each hollow knife. A yoke 17 of rod-shaped material is fixedly mounted on the body 2 above the valve arrangements and extends throughout half a revolution of the sticking carousel on the side thereof facing the blood withdrawing zone.

Figure 3A:
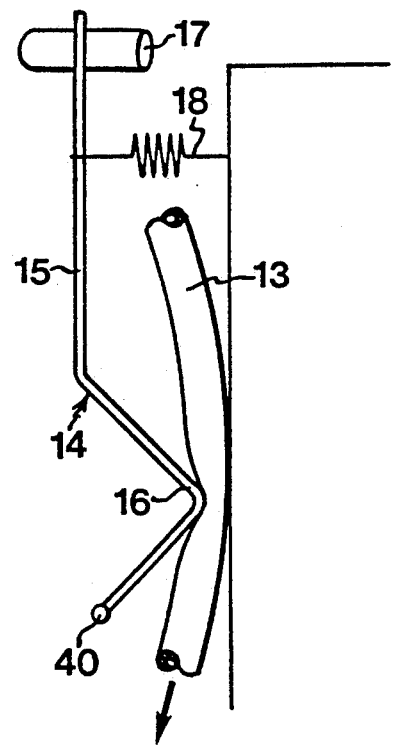
FIG. 3a is an enlarged detail view at III in FIG. 2.

FIG. 3a shows the design and the operation of each valve arrangement. The valve arrangement 14 has a valve arm 15 whose one end is pivotable in a vertical plane about a shaft 40 mounted on the movable part of the sticking carousel. A spring 18 is connected between the valve arm and the movable part of the sticking carousel and biases the valve arm in the direction of the rotary shaft of the sticking carousel. Between the mounting point of the spring and the shaft 40, the valve arm has an angled actuator portion 16. In FIG. 3, the spring 18 pulls the actuator portion of the valve arm into engagement with the anticoagulant hose 13 for compressing it in order to interrupt the supply of anticoagulant to the hollow knife. This closure is effected at the end of the blood withdrawing zone where the yoke has been brought out of its engagement with the upper end of the valve arm. On the diametrically opposite side of the sticking carousel, the valve arm is moved into engagement with the yoke 17 and is pivoted radially outwards. This pivotal movement permits opening the hose 13. Anticoagulant is now allowed to pass through the hose to the hollow knife. The hose is held open as long as the valve arm is maintained in its outwardly-pivoted position by means of the yoke 17.

Figure 3B:
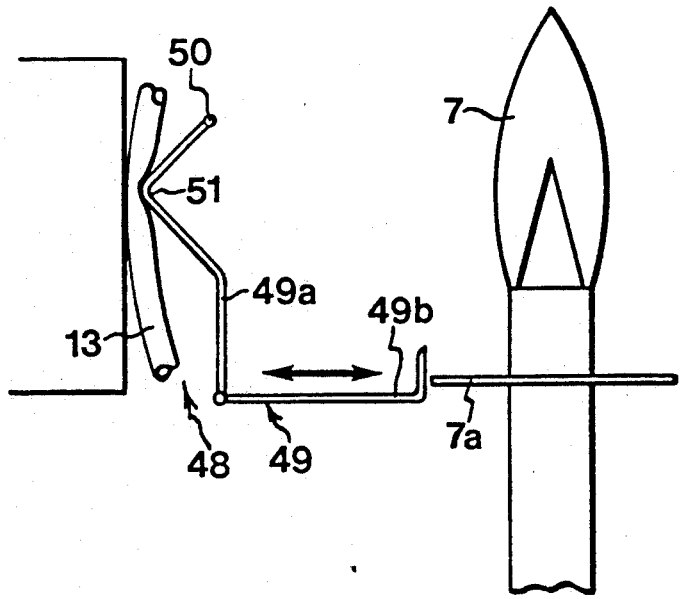

Normally, the slaughter animals are practically evenly distributed on the conveyor. Sometimes, however, it happens that there are gaps or voids on the conveyor, which means that some hollow knife is not being used but remains hanging in its holder. In this case, anitcoagulant should of course not be supplied to the hollow knife. The valve arrangement 48 in FIG. 3b is designed to cope with this problem. This valve arrangement consists of a valve arm 49 which is pivotable at its upper end in a vertical plane about a shaft 50. This shaft is mounted in the rotary part of the sticking carousel. The valve arm has a vertical part 49a with an actuator portion 51, and a horizontal part 49b adapted to be acted on by the hollow knife when it is suspended in its holder. The Figure schematically shows the hollow knife 7 in its suspended position, but does not show the holder. When the hollow knife is placed in the holder, the drip ring 7a of the hollow knife is brought into engagement with the part 49b of the valve arm so as to urge the actuator portion 51 against the hose 13. When the hollow knife is removed from its holder, the pressure in the hose and the inherent elasticity of the hose will cause the valve arm to pivot radially outwards from the shaft of the sticking carousel. If required, a compression spring may be mounted between the valve arm and the sticking carousel. In this embodiment, the yoke 17 in FIG. 2 is of course excluded.

FIG. 4 shows an example of a washing or cleaning unit 19 which is modified as compared with that shown in FIG. 1. For greater clarity, most of the parts of the sticking carousel have been removed. In the Figure, there are shown a collecting vessel 6, a hose 8 and a hollow knife 7 with its holder 9. The washing pipe 24 with the associated spray nozzle 27 is also shown in the Figure.

The cleaning unit 19 consists of a washing box 20 which is raisable and lowerable by operating means (not shown). The cleaning unit is disposed above the upper frame member and aligned with one of the stopping positions of the holders 9. The washing box 20 may be cylindrical or have any other suitable shape. Two spray nozzles 21 are mounted in the washing box and connected to a conduit 41 for sterilising liquid which after each use of the hollow knife is sprayed against it. In this embodiment, the pipe 22 in FIG. 1A is connected to the washing box 20 and adapted to supply a major amount of cleaning liquid for sterilising and washing the hollow knife, the hose and the collecting vessel. For cleaning the collecting vessel, there is provided a second pipe 23 connected to the first pipe 22. As mentioned above, the second pipe 23 will dock the pipe 24 when the cleaning unit 19 is lowered. This more complete cleaning is not performed after each sticking operation, but normally after a batch is completed.

FIG. 5 shows an embodiment using the cleaning unit 19. This Figure shows a sticking carousel from above and illustrates three cleaning units 19 disposed after each other. The Figure does not show the conduits 41, 22 and 23. Each washing box of the cleaning unit is disposed above one of the stopping positions of the holders for the hollow knives. At the centre of the sticking carousel, the arrow indicates the direction of rotation of the carousel, which in this case is counter-clockwise. The Figure also shows a washing and sterilising zone.

The cleaning units are lowered each time the carousel is rotated one step. Cleaning or sterilisation of the hollow knife after each sticking operation can be carried out in the following manner. In the first washing box (to the left in the Figure), the knife is washed with water having a temperature of about 30° C. In the second washing box, the knife is sterilised with water having a temperature of about 82° C. In the third washing box, finally, the knife is cooled with water having a temperature of about 10° C. Liquids other than water may of course also be used for cleaning.

Figure 1B:
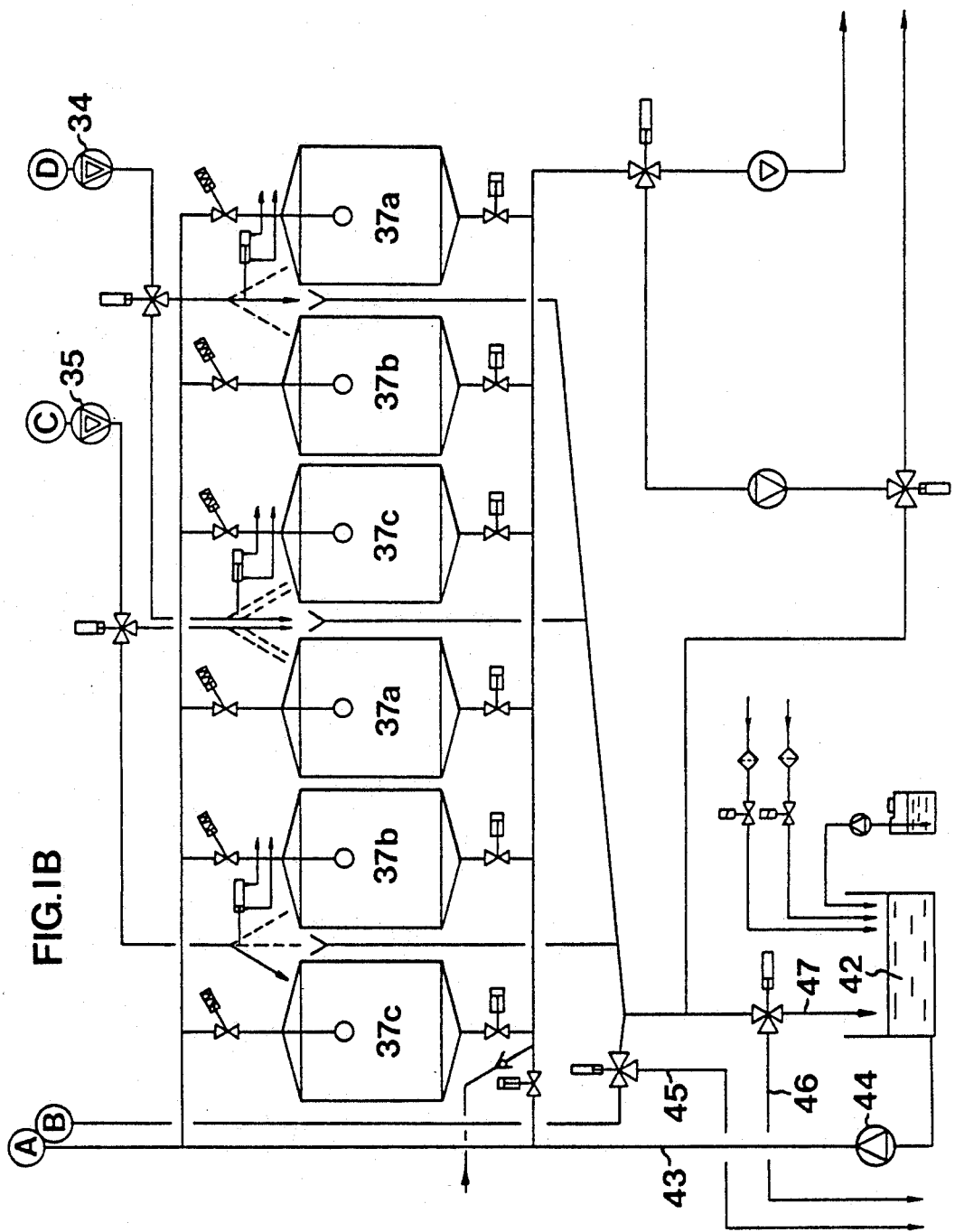

FIGS. 1A and 1B also illustrate a central cleaning plant connected to all the parts of the sticking plant which require cleaning. The cleaning plant being no part of the invention, it will be only briefly described below.

The cleaning plant includes a tank 42 containing cleaning liquid. Cleaning liquid can be pumped from this tank through a conduit 43 by means of a pump 44 to the washing or cleaning units in the sticking carousel, to the discharge conduits 30 and 31 below the collecting vessels, to the equaliser tanks 32 and 33 and to the storage vessels 36a-c and 37a-c. After the entire equipment has been cleaned, the cleaning liquid can be fed to a drain (not shown) through a conduit 45 or 46, these conduits being connected to the above-mentioned parts of the plant. It is also possible to recycle the cleaning liquid in the system through a recycling conduit 47.

The operation of the device according to the invention will now be described.

The sticker takes a hollow knife from its holder in the sticking carousel at the beginning of the blood withdrawing zone and sticks it into an animal. Thanks to the special design of the knife, it remains in the sticking wound during the rotation of the carousel through half the revolution which is covered by the blood withdrawing zone. A helper who is standing at the end of the blood withdrawing zone removes the hollow knife from the animal and hangs it up in the carousel. Now, the blood is in the collecting vessel, and anitcoagulant has been automatically supplied to the hollow knife during the blood withdrawing operation. When the knife is placed in its holder, the carousel is rotated one step. After each sticking operation, the hollow knife is automatically washed by means of cleaning units above the sticking carousel. After each completed batch, corresponding to between 40 and 120 animals, both the knife, the hose and the collecting vessel are automatically washed.

The extracted blood is automatically emptied into a funnel connected to one the two discharge conduits 30 and 31, and the blood is conducted to one of the storage vessels 36a-c, 37a-c selected by the control system. When one discharge conduit with the associated storage vessel should be cleaned, the control system automatically switches to the other discharge conduit.

When the last animal in a batch has passed a veterinary inspection station, the corresponding storage vessel is automatically emptied, either in a tank for accepted blood or in a tank for rejected blood.

After each emptying of rejected blood, the corresponding storage vessel is automatically cleaned. After emptying of accepted blood, the storage vessel is optionally subjected either to a brief flushing with cold water or to complete cleaning.

I claim:

1. Device for withdrawing blood from slaughter animals transported on a conveyor serially past a sticking station, said device having a carousel (1) disposed at said sticking station and including a body (2), a lower frame member (3) and an upper frame member (4), said frame members being synchronously rotatable on a vertical shaft (5) of said body, a number of collecting vessels (6) mounted on the lower frame member around said vertical shaft, a number of hollow knives (7) corresponding to the number of collecting vessels and suspendible around said vertical shaft each in a holder (9) on said upper frame member, and a hose (8) extending between each hollow knife and the associated collecting vessel for conducting blood from the hollow knife to the collecting vessel, characterised in that the carousel (1) is rotatable in such steps that the holders (9) are displaced between a number of stopping positions around said vertical shaft, the distance between said stopping positions being equal to the distance between said holders; and that a sensor (10) is fixedly mounted on said body (2) opposite one of said stopping positions and adapted to sense the displacement of a hollow knife (7) in a holder located in this stopping position, in order upon such displacement to initiate rotation of the carousel one step.

2. Device as claimed in claim 1, characterised in that the sensor (10) is adapted to sense the suspension of the hollow knife (7) in the holder (9).

3. Device as claimed in claim 1, characterised by means for supplying an anticoagulant to the hollow knife (7), said means comprising a supply conduit (11) extending between a store of anticoagulant (12) and said carousel (1), flexible anticoagulant hoses (13) extending from said supply conduit to each hollow knife, and a valve arrangement (14) connected to each such anticoagulant hose and maintaining the anticoagulant hose open when the hollow knife is stuck into an animal, and closed when the hollow knife is suspended in its holder (9).

4. Device as claimed in claim 3, characterised in that the valve arrangement (14) has a valve arm (15; 49) pivotable in a vertical plane and having an actuator portion (16; 51) which is pivotable into and out of engagement with said anticoagulant hose (13) for closing and opening this hose.

5. Device as claimed in claim 4, characterised in that the valve arm (49) is operable by means of the hollow knife (7) which when suspended in its holder urges said valve arm against the anticoagulant hose (13) for closing it, and when unhooked from its holder permits pivoting the valve arm away from the anticoagulant hose for opening it.

6. Device as claimed in claim 5, characterised in that the valve arrangement has operating means (17) mounted on said body (2) in the area of movement of said valve arm (15) in order, during a part of the revolution of the carousel (1), to move the valve arm, by engaging it, out of engagement with the anticoagulant hose (13) against the action of a spring (18) connecting the valve arm to the carousel.

7. Device as claimed in claim 6, characterised in that said operating means is a horizontal yoke (17) extending throughout 180° of the carousel (1).

8. Device as claimed in claim 1, characterised by a cleaning unit (19) which is vertically movably mounted on the body (2) above at least one stopping position of said holders (9) and has at least one washing box (28, 29; 20) and at least one first spray nozzle (21) mounted in the washing box, said washing box being adapted, when the cleaning unit is lowered, to enclose a hollow knife (7) suspended in a holder (9) and said spray nozzle being adapted to spray cleaning liquid against the hollow knife.

9. Device as claimed in claim 8, characterised by a first pipe (22) connected to the washing box (20) for supplying cleaning liquid thereto and, via the hollow knife (7), through the hose (8) down to the collecting vessel (6).

10. Device as claimed in claim 9, characterised by a second pipe (23) connected to said first pipe (22) and adapted, when the cleaning unit (19) is lowered, to dock a third tube (24) connected to a second spray nozzle (27) in the collecting vessel (6).

11. Device as claimed in claim 1, characterised by a quantity sensor (25) mounted in the collecting vessel (6) and adapted to sense the amount of blood in the collecting vessel and to initiate an alarm if the amount of blood falls below a given threshold value.

* * * * *